United States Patent [19]

Hutson, Jr.

[11] 4,262,155
[45] Apr. 14, 1981

[54] MAXIMIZATION OF ISOPARAFFIN UTILIZATION IN ALKYLATION OF HYDROCARBONS

[75] Inventor: Thomas Hutson, Jr., Bartlesville, Okla.

[73] Assignee: Phillips Petroleum Company, Bartlesville, Okla.

[21] Appl. No.: 54,530

[22] Filed: Jul. 3, 1979

[51] Int. Cl.³ .......................... C07C 2/20; C07C 2/58
[52] U.S. Cl. ................... 585/329; 585/331; 585/701; 585/709; 585/717
[58] Field of Search ............... 585/709, 701, 717, 332, 585/331, 329

[56] References Cited

U.S. PATENT DOCUMENTS

| | | | |
|---|---|---|---|
| 2,338,272 | 1/1944 | Westenberg | 585/717 |
| 2,554,275 | 5/1951 | Smith | 585/331 |
| 2,563,051 | 8/1951 | Linn | 585/331 |
| 2,881,235 | 4/1959 | Van Pool | 585/701 |
| 2,990,437 | 6/1961 | Berger | 585/701 |
| 3,309,420 | 3/1967 | Van Pool | 585/701 |

Primary Examiner—Curtis R. Davis

[57] ABSTRACT

Utilization of isoparaffin is maximized in an alkylation of isoparaffin with olefin by variously detecting and/or measuring change in amount of hydrocarbon effluent, the alkylation zone and supplying a sufficient amount of olefin to said alkylation zone to keep the amount of hydrocarbon effluent said alkylation zone substantially constant, in one embodiment sensing the level of hydrocarbon in a settling zone in which alkylation zone effluent is settled, said level being representative of the amount of hydrocarbon being formed, and increasing the amount of olefin when effluent the alkylation zone is increasing, and vice versa.

6 Claims, 3 Drawing Figures

MAXIMIZATION OF ISOPARAFFIN UTILIZATION IN ALKYLATION OF HYDROCARBONS

BRIEF SUMMARY OF THE INVENTION

In one of its aspects, the invention relates to the alkylation of hydrocarbons. More particularly, the invention relates to the alkylation of an isoparaffin with an olefin. Further, it relates to the maximization of utilization of isoparaffin in the alkylation of an isoparaffin with an olefin.

In one of its concepts, the invention provides a process for the alkylation of an isoparaffin with an olefin which comprises detecting the amount of hydrocarbon effluent the alkylation zone and adjusting the ratio of olefin to isoparaffin fed to said zone responsive to change in the detected amount of hydrocarbon, i.e., increasing the amount of olefin whenever the detected amount of hydrocarbon is increasing and decreasing the amount of olefin whenever the detected amount of hydrocarbon is decreasing. In another of its concepts, the invention provides such a process as herein described wherein, in usual alkylation system, in a settler in which the hydrocarbon phase and catalyst phase are formed and from which hydrocarbon phase and acid phase are withdrawn at a substantially constant rate, the level of the hydrocarbon phase in the settler is detected and the olefin to isoparaffin ratio adjusted according to whether the level of the hydrocarbon phase is increasing or decreasing, i.e., increasing the amount of olefin fed to the alkylation zone when the hydrocarbon phase level is increasing and vice versa. In a further concept of the invention there is provided a process in which a combination of operations is effected—an alkylation and a dimerization—and wherein an olefin containing feed, which may also contain some isoparaffin, is in part fed to the alkylation and in part fed to the dimerization; the dimerization being conducted to produce dimers which are advantageously incorporated into the final hydrocarbon product of the process. In a further concept of the invention still, as later described in more detail, there is provided in said combination a fractionation zone in which preliminarily there is fractionated a saturated isoparaffins-containing feed and to which an olefins-containing feed, also containing some isoparaffin, can be and is, at least in part, fed depending upon the controlled desired ratio of the olefin to isoparaffin in the alkylation zone, the operation being so set up and conducted that isoparaffin is utilized to a maximum regardless of its source to the operation and regardless of wherein the operation it is found or recovered.

The above and additional concepts of the invention, as these may be viewed are based upon the knowledge that there is always to be maintained, as far as possible, a desirable ratio of isoparaffin to olefin in the alkylation reaction zone and that whenever this ratio changes there is either a net consumption of isoparaffin reducing the desired ratio or isoparaffin is not being utilized at maximum utilization capacity.

An object of this invention is to produce a high-octane alkylate hydrocarbon product. Another is to maximize utilization of isoparaffin without loss of the desired ratio of isoparaffin to olefin in the alkylation reaction zone. A further object is to alkylate with preferred olefin e.g. butene-2, while maximizing the isoparaffin utilization and maintaining the desired optimum isoparaffin-to-olefin ratio in the alkylation reaction zone. A still further object of the invention is to provide a combination of steps in operation in which there can be concomminent maximization of isoparaffin utilization and optimum utilization of olefin in an olefin-containing stream fed to the process. Still another object of the invention is to provide an operation in which suitable control can be exercised to utilize to best advantage olefins fed to the process while maximizing utilization of isoparaffin regardless of the source of isoparaffin which enters into the process.

Other aspects, concepts, objects, and the several advantages of the invention are apparent from a study of this disclosure, the drawings, and the appended claims.

DETAILED DESCRIPTION

According to the present invention, there is provided a process in which any increase or decrease of hydrocarbon in the alkylation zone effluent is detected or monitored and utilized to adjust the isoparaffin-to-olefin ratio in said alkylation zone to maximize utilization of isoparaffin, e.g. isobutane therein.

Also according to the present invention, there is provided a process comprising the steps of feeding isoparaffin and an olefins-containing stream, also containing some isoparaffin to an alkylation zone, removing alkylation effluent from said zone, fractionating said effluent, obtaining an isoparaffin stream, recycling said isoparaffin stream to said alkylation zone; also feeding at least a portion of said olefins-containing stream to a dimerization zone, dimerizing olefins contained in said stream in passing dimerization zone effluent to said fractionation zone and withdrawing from said fractionation zone a stream containing alkylate and dimer; detecting the amount or degree of utilization of isoparaffin in said alkylation zone and adjusting the amounts of olefins-containing stream fed to said alkylation zone and to said dimerization zone respectively, i.e., increasing the amount of olefin fed to said alkylation zone when hydrocarbon generated therein is increasing and decreasing the amount of olefin fed to said zone when hydrocarbon generated therein is decreasing and in each case passing the remainder of the olefins-containing stream to said dimerization zone and so operating independently from the amount of recycle isoparaffin stream being fed to said alkylation zone which, in a preferred operation, will be maintained to process maximum available recycle isoparaffin.

Still according to the present invention there is provided an operation as described herein wherein there is provided a fractionation or splitter zone in combination with an alkylation zone and a dimerization zone and wherein the amount of olefins-containing stream fed to said splitter zone and to said alkylation zone and from said splitter zone to said dimerization zone is, for each stream, adjusted, ultimately, according to the amount of hydrocarbon being generated in the alkylation zone, also as herein described.

Still according to the present invention there is provided a process as herein described wherein the amount of hydrocarbon generated in the alkylation zone is detected as by measuring the level thereof in a settling zone in which hydrocarbon phase and catalyst phase are settled and separated and in which, in a preferred form of operation, the acid phase is maintained on a liquid level control and hydrocarbon phase is withdrawn at a constant flow rate thus enabling to more precisely measure the amount of hydrocarbon generated and thus to control the operation as herein described.

Figure 1:
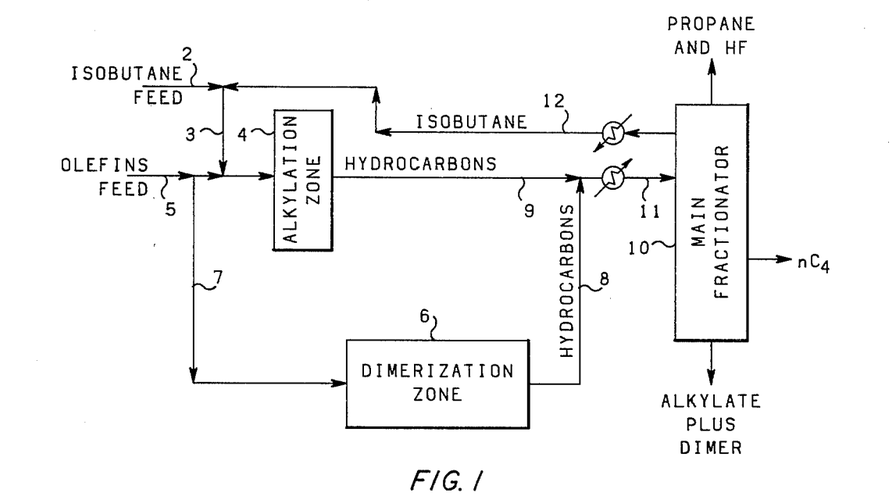
FIG. 1 diagrammatically illustrates an operation to which isoparaffin, e.g., a stream containing isobutane, is fed to an alkylation zone together with an olefin containing stream, the stream also containing isoparaffin and wherein the reaction effluent from an alkylation zone is passed through a fractionation zone; the amount of olefin passed through the alkylation zone being controlled as herein described and olefin not needed in the alkylation zone is passed through a dimerization zone effluent from which is also passed to the fractionation zone in which isoparaffin is recovered and from which recovered isoparaffin is recycled to the alkylation zone for maximum utilization there as herein described.

Referring now to the drawing in FIG. 1, an isobutane containing stream, obtained as from a field butanes splitter is fed by 2 and 3 to alkylation zone 4 wherein it is alkylated with olefin in an olefins-containing stream, also containing some isoparaffin, fed by 5 to said alkylation zone. Dimerization zone 6 is provided to dimerize olefins in the olefins-containing stream fed to it by 5 and 7. Dimer containing product is fed by 8 together with alkylation zone effluent fed by 9 to main fractionator 10 by conduit 11. For sake of simplicity, in this figure of the drawings, the usual settling or hydrocarbon from catalyst separation zone or vessel has been omitted. Thus, it will be understood that the main fractionator 10 processes only the hydrocarbon phase from the alkylation zone.

All of the available, recoverable isoparaffin is removed from fractionator 10 and passed by 12 and 3 to the alkylation zone 4. It is this recycle isoparaffin or isobutane that is utilized to a maximum by detecting the amount of hydrocarbon being formed in the alkylation zone and adjusting the amount of olefins-containing stream fed into the alkylation zone to there suitably alkylate the isoparaffin while at the same time maintaining a desirable isoparaffin-to-olefin ratio.

Figure 2:
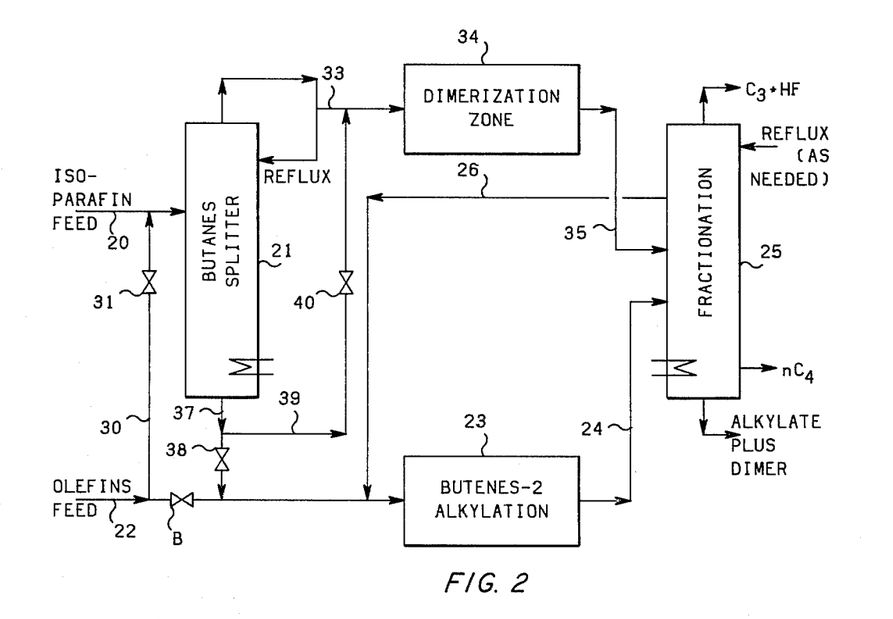
FIG. 2 diagrammatically illustrates a combination of the invention as herein described in which the arrangement is modified to include a preliminary fractionation zone or splitter in which iso- and normal paraffins mixture is fractionated and in which, as desired at least a portion of the olefin-containing feed, also containing isoparaffin, can also be fractionated and from which olefin can be passed to alkylation and/or to dimerization while at least in one aspect of the operation an olefin containing stream is fed directly into the alkylation and in another aspect of the operation is fed in part to the splitter and to the alkylation.

Referring now to FIG. 2, an isoparaffin containing stream 20 is fed to splitter 21. An olefins-containing stream, also containing isoparaffin, is fed by 22 to alkylation zone 23. Effluent 24 from the alkylation zone is passed to a main fractionation zone 25 from which a recycle isoparaffin or isobutane stream 26 is returned to alkylation zone 23.

Olefin not needed in alkylation zone 23 to there maximize utilization of isoparaffin can be passed by 30 and valve 31 to splitter 21. Splitter 21 is so operated as to obtain overhead therefrom a substantial portion of butene-1, while obtaining as bottoms therefrom a stream containing butene-2, an advantageous alkylating agent. The overhead from splitter 21 is passed by 33 to dimerization zone 34 and dimer, together with isoparaffin or isobutane, is passed by 35 to fractionation zone 25.

Bottoms from splitter 21, containing butene-2, are withdrawn by 37 through valve 38 and passed by 22 to alkylation zone 23.

A cross-over conduit 39 having valve 40 connects conduit 37 from a point ahead of that valve 38 to conduit 33.

In the event maximization of isobutane is not optimum, valve 31 can be opened or further opened as the case may be and valve B throttled or shut down. It is possible within the scope of the invention to provide all of the olefin to alkylation zone 23 by way of splitter 21 when valve 38 will be opened to supply the desired amount of olefin to zone 23.

Whenever there is an excessive amount of olefin passing to alkylation zone 23 and, in its preferred form of operation valve 31 is open and valve B in line 22 is closed or substantially closed, valve 38 can be throttled down and valve 40 opened to permit the portion of olefin not desired in alkylation zone 23, at least for the moment, to pass to dimerization zone 34.

It will be noted by one skilled in the art, in possession of this disclosure, having studied the same, that in any event high-grade product is produced from all of the isoparaffin and from the olefin fed to the operation there being obtained from fractionation zone 25 high-quality alkylate containing dimer produced in dimerization zone 34.

Figure 3:
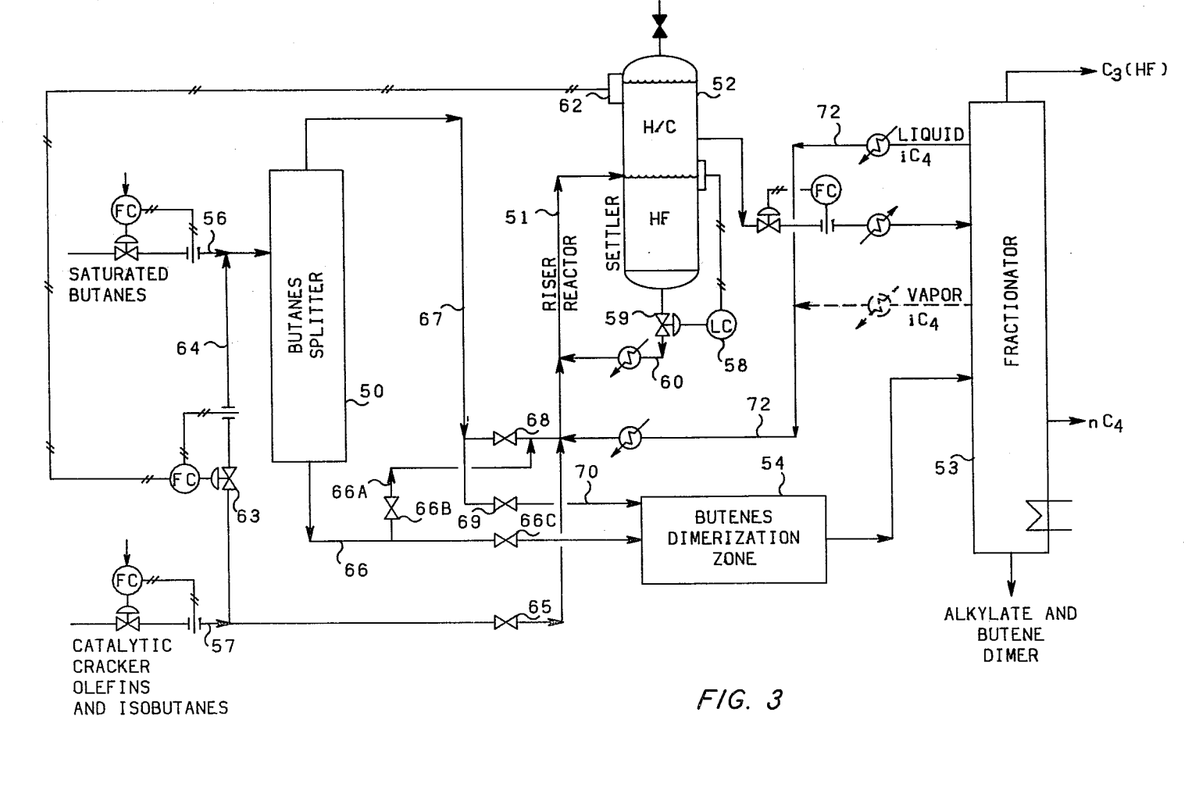
FIG. 3 diagrammatically illustrates a combination operation in which the hydrocarbon effluent the alkylation zone is measured or detected as by a liquid level sensing device and the ratio of isobutane-to-olefin in the alkylation zone is maintained to maximize utilization of isoparaffin therein.

Referring to FIG. 3 there are shown a butanes splitter 50, a riser reactor alkylation zone 51, a settler zone 52, a main fractionator zone 53 and a dimerization zone 54.

A stream containing isobutane and normal butane is fed by 56 to splitter 50. A catalytic cracker olefins-containing stream, also containing isobutane, is fed by 57 to riser reactor alkylation zone 51. The usual alkylation conditions are maintained in zone 51 in which a liquid, e.g., a hydrofluoric acid catalyst is employed. The effluent from zone 51 is passed to settler zone 52 wherein hydrocarbon phase and acid phase are separated. The acid phase is maintained on liquid level control, the liquid level controller 58 which controls valve 59 in 60 by way of which the acid is returned to the riser reactor zone 51. Liquid level sensing device 62 transmits a signal to flow control valve 63 in conduit 64. Valve 63 is adjusted by way of the signal to pass into butane splitter 50 olefin not needed and not desired in riser reactor 51. Thus, when the level of hydrocarbon in vessel 52 tends to fall, indicating an undesired lowering of the isobutane-to-olefin ratio in the riser reactor valve 63 will be open. Conversely, when the level of hydrocarbon phase in vessel 52 is tending to increase, indicating inefficient or nonmaximum utilization of isoparaffin or isobutane, valve 63 will be throttled down, or closed, feeding more olefin directly to riser reactor 51.

In a now particular embodiment of the invention there is provided a valve 65 in line 57. By throttling down valve 65, or closing the same, thus tending to lower the amount of olefin available to riser reactor 51 thus tending to build up hydrocarbon phase in vessel 52 will cause valve 63 to open which in turn will cause increased generation of olefin in butanes splitter 50 bottoms 66 rich in butenes-2 which are passed to alkylation 51 by 66A. This is the most desirable operation. In the event additional olefin is still needed in riser reactor 51 overhead from splitter 50 can be passed by 67 and valve 68 to riser reactor 51. Normally, it will be preferred to dimerize any unneeded light olefins, e.g., butene-1. For this, valve 68 will be closed and valve 69 in line 70 will be opened, thus conducting the olefins to the butene dimerization zone.

In this preferred embodiment the level controller 62 does not now actuate valve 63, but valve 63 is fully opened and valve 65 is fully closed so that the butenes stream 57 is charged via 64 to splitter 50, yielding butenes-2 concentrate 66 and butene-1 concentrate 67. Valves 66B, 66C (opposite acting) are controlled by the low range of a now used split-range level controller 62, and valves 68 and 69 (opposite acting) are controlled by the high range of the split-range level controller 62.

To illustrate the control operation, using the now split-range level controller 62 to actuate opposite acting valves 66B and 66C (actuated in response to the low range of the split-range level controller 62) and to actuate opposite acting valves 68 and 69 (actuated in response to the high range of the split-range level controller 62), if the level in 52 tries to rise, valve 66B is further opened and valve 66C is further pinched down, charging additional butenes-2 to alkylation, as desired; if the level in 52 continues to try to rise, valve 66B will become fully opened and valve 66C will become fully closed, flowing all of the butenes-2 stream 66 to alkylation; if level in 52 still tries to rise, the upper range control of split-range level controller 62 takes over opening now valve 68 and pinching down on valve 69, to flow butene-1 from line 67 to alkylation, until the level in 52 is attained. And if the level in 52 tries to decrease, a reverse operation is effected so that maximum utilization of feed isobutane is effected with high octane alkylate former butenes-2 will be charged to alkylation, the remainder or excess butenes being charged to dimerization.

It will be seen, upon study of the drawing, that all available and recoverable isoparaffin passes from fractionator 53 by 72 to riser reactor 51.

The following examples have been calculated to further illustrate the operation of the invention.

In all examples, alkylate was calculated as 1.76 times olefin alkylated, and dimer was calculated as 0.7 times olefin dimerized.

EXAMPLE I

See FIG. 1.

Run I (A) is an initial operation wherein the total alkylate yield is 810.9 barrels per hour. Fresh or feed isobutane is 71 barrels per hour. Olefin feed is 81 barrels per hour. The olefin is split so only 71 barrels per hour is charged to alkylation, with 10 barrels per hour to dimerization. Isobutane to olefin volume ratio is 10 to 1, with 639 barrels per hour of recycle isobutane.

Run II (B) has an increase of olefin in the feed, and does not use the invention. The same flow of split olefins is required, as in Run I, without the invention. Feed isobutane is 67 barrels per hour, but olefin to alkylation is now 88 barrels per hour, or each hour 78-67 or 11 barrels per hour of recycle isobutane is used up. Ultimately there will be no recycle isobutane. On the first cycle, or first hour, recycle isobutane falls from 639 barrels per hour to about 628 barrels per hour, and total alkylate yield falls from 810.9 barrels per hour to 808.9 barrels per hour. The isobutane to volume ratio after one hour is about 9.16 to 1.

Run III (C) has the same increase in olefin as Run II, but applies the invention which maintains the alkylation yield at 810.9 barrels per hour. Run III adjusts the quantities of olefin split between alkylation and dimerization. Run III is an illustrative "spot" run. That is, as the amount of alkylation yield tries to fall below 810.9 barrels per hour, less olefin is fed to alkylation. Feed isobutane will be greater than needed for olefin in alkylation. In this manner isobutane recycle is increased to account for losses in the feed to alkylation, and maintains the alkylation yield at 810.9 barrels per hour. Ultimately, the recycle isobutane will tend to be too high and the tendency for total alkylation yield to go above 810.9 barrels per hour will be accounted for by more olefin being charged to alkylation, thusly to hold total alkylate yield at 810.9 barrels per hour.

EXAMPLE 1

| | Field Butanes to Alky | Olefins | Olefins to Alky | Olefins to Dimer | Recycle Isobutane | Total to Alky | Alky Yield | Yield Dimer | Total to Fract | Gaso Yield | Normal Butane |
|---|---|---|---|---|---|---|---|---|---|---|---|
| (A) Stream Number Component | | | | | (Barrels/Hour) | | | | | | |
| (I) | | | | | | | | | | | |
| Isobutane | 61 | 10 | 8.8 | 1.2 | 640.2 | 710 | 639 | 1.2 | 640.2 | — | — |
| Isobutylene | — | 21 | 18.4 | 2.6 | — | 18.4 | — | — | — | — | — |
| Butene-1 | — | 30 | 26.3 | 3.7 | — | 26.3 | — | — | — | — | — |
| Normal Butane | 39 | 9 | 7.9 | 1.1 | — | 46.9 | 46.9 | 1.1 | 48 | — | 48 |
| Butenes-2 | — | 30 | 26.3 | 3.7 | — | 26.3 | — | — | — | — | — |
| Alkylate | — | — | — | — | — | — | 125 | — | 125 | 125 | — |
| Dimer | — | — | — | — | — | — | — | 7 | 7 | 7 | — |
| TOTAL | 100 | 100 | 87.7 | 12.3 | 640.2 | 827.9 | 810.9 | 9.3 | 820.2 | 132 | 48 |
| Isobutane | 61 | 10 | 8.8 | 1.2 | 640.2 | 710 | 639 | 1.2 | 640.2 | 0 | 0 |
| Olefins | 0 | 81 | 71 | 10 | — | 71 | 0 | 0 | 0 | 0 | 0 |
| (IC$_4$/Olefin Vol) | — | — | — | — | — | (10/1) | — | — | — | — | — |
| (B) Olefin Composition changed without invention Operation | | | | | | | | | | | |
| Isobutane | 61 | 6 | 5.3 | 0.7 | 639.7 | 706 | 628.9 | 0.7 | 629.6 | — | — |
| Isobutylene | — | 24 | 21.0 | 3 | — | 21 | — | — | — | — | — |

EXAMPLE 1-continued (Barrels/Hour)

| | Field Butanes to Alky | Olefins | Olefins to Alky | Olefins to Dimer | Recycle Isobutane | Total to Alky | Alky Yield | Yield Dimer | Total to Fract | Gaso Yield | Normal Butane |
|---|---|---|---|---|---|---|---|---|---|---|---|
| Butene-1 | — | 34 | 29.8 | 4.2 | — | 29.8 | — | — | — | — | — |
| Normal Butane | 39 | 6 | 5.3 | 0.7 | — | 44.3 | 44.3 | 0.7 | 45 | — | — |
| Butenes-2 | — | 30 | 26.3 | 3.7 | — | 26.3 | — | — | — | — | 45 |
| Alkylate | — | — | — | — | — | — | 135.7 | — | 135.7 | 135.7 | — |
| Dimer | — | — | — | — | — | — | — | 7.6 | 7.6 | 7.6 | — |
| TOTAL | 100 | 100 | 87.7 | 12.3 | 639.7 | 827.4 | 808.9 | 9.0 | 817.9 | 143.3 | 45 |
| Isobutane | 61 | 6 | 5.3 | 0.7 | 639.7 | 706 | 628.9 | 0.7 | 629.6 | 0 | 0 |
| Olefins | 0 | 88 | 77.1 | 10.9 | 0 | 77.1 | 0 | 0 | 0 | 0 | 0 |
| (IC$_4$/Olefin Vol) | — | — | — | — | — | (9.16/1) | — | — | — | — | — |
| (C) Olefin Composition as in II with Invention's Operation | | | | | | | | | | | |
| Isobutane | 61 | 6 | 3 | 3 | 692.9 | 735.5 | 691.5 | 3 | 649.5 | — | — |
| Isobutylene | — | 24 | 12 | 12 | — | 12 | — | — | — | — | — |
| Butene-1 | — | 34 | 17 | 17 | — | 17 | — | — | — | — | — |
| Normal Butane | 39 | 6 | 3 | 3 | — | 42 | 42 | 3 | 45 | — | 45 |
| Butenes-2 | — | 30 | 15 | 15 | — | 15 | — | — | — | — | — |
| Alkylate | — | — | — | — | — | — | 77.4 | — | 77.4 | 77.4 | — |
| Dimer | — | — | — | — | — | — | — | 30.8 | 30.8 | 30.8 | — |
| TOTAL | 100 | 100 | 50 | 50 | 692.9 | 821.5 | 810.9 | 36.8 | 847.7 | 108.2 | 45 |
| Isobutane | 61 | 6 | 3 | 3 | 692.9 | 735.5 | 691.5 | 3.0 | 694.5 | 0 | 0 |
| Olefins | 0 | 88 | 44 | 44 | — | 44 | 0 | 0. | 0 | 0 | 0 |
| (IC$_4$/Olefin Vol) | — | — | — | — | — | (16.72/1) | — | — | — | — | — |

EXAMPLE 3

See FIG. 3.

Run I (A) is an initial operation wherein the total alkylate yield is 770 barrels per hour. The split of the olefin is 33.33 percent to fractionation and 66.67 percent by-pass to alkylation. Feed isobutane is 71 barrels per hour requiring 71 barrels per hour olefins for alkylation, leaving 10 barrels per hour excess olefin for dimerization. Total alkylation yield is 770 barrels per hour. Isobutane to olefin volume ratio is 10 to 1, with 639 barrels per hour of recycle isobutane.

Run II (B) has an increase of olefin in the feed, and does not use the invention. The same split of 33.33 percent of olefin feed to fractionation and 66.67 percent by-pass to alkylation, as in Run I, is required without the invention. Feed isobutane is 67 barrels per hour, but olefin to alkylation is now 78 barrels per hour, or each hour 78–67 or 11 barrels of recycle isobutane is used up. Ultimately (in about 58 hours, there will be no recycle isobutane). On the first cycle, or first hour, recycle isobutane drops from 639 to 628 barrels per hour. Total alkylation yield drops from 770 to 769.3 barrels per hour or a 0.7 barrel decrease in the first hour. Isobutane to olefin volume ratio goes, in first hour, to 9.06 to 1.

Run III (C) has the same increase in olefin as Run II, but applies the invention which maintains the alkylation yield at 770 barrels per hour. Run III adjusts the quantities of olefin split between the fractionator and the by-pass to alkylation. The Run III is an illustrative "spot" run. That is, as the amount of alkylation yield tries to fall below 770 barrels per hour, less olefin is fed to alkylation, allowing isobutane recycle to increase to account for losses in feed to alkylation. In order for isobutane to build up, less olefin than the feed isobutane is charged to alkylation. This operation maintains the total alkylation yield at 770. However, when the recycle isobutane tends to increase too much which actuates some more olefin to pass to alkylation, but still maintaining 770 barrels per hour total alkylate to maximize use of feed isobutane in alkylation.

EXAMPLE 3

(Barrels/Hour)

| (A) STREAM NUMBER COMPONENT (I) | Field Butanes | Olefins | Olefins to Fractionation | Olefins By Pass | Fractionator Overhead | Fractionator Bottoms | Fresh Feed to Alkylation | Isobutane Recycle |
|---|---|---|---|---|---|---|---|---|
| Isobutane | 61 | 10 | 3.33 | 6.67 | 64.33 | — | 71 | 639 |
| Isobutylene | — | 21 | 7 | 14 | 7 | — | 21 | — |
| Butene-1 | — | 30 | 10 | 20 | 10 | — | 30 | — |
| Normal Butane | 39 | 9 | 3 | 6 | — | 42 | 6 | — |
| Butenes-2 | — | 30 | 10 | 20 | — | 10 | 20 | — |
| Alkylate | — | — | — | — | — | — | — | — |
| Dimer | — | — | — | — | — | — | — | — |
| Total | 100 | 100 | 33.33 | 66.67 | 81.33 | 52 | 148 | 639 |
| Isobutane | 61 | 10 | 3.33 | 6.67 | 64.33 | 0 | 71 | 639 |
| Olefins | 0 | 81 | 27 | 54 | 17 | 10 | 71 | 0 |
| (IC$_4$/Olefin vol) | — | — | — | — | — | — | — | — |
| | | Total | | Total | | | | |

EXAMPLE 3-continued (Barrels/Hour)

| (A) | | To Alkylation | Alky Yield | Dimer Yield | To Main Fractionation | Gasoline Yield | Normal Butane |
|---|---|---|---|---|---|---|---|
| STREAM NUMBER COMPONENT | | | | | | | |
| (I) | | | | | | | |
| Isobutane | | 710 | 639 | — | 639 | — | — |
| Isobutylene | | 21 | — | — | — | — | — |
| Butene-1 | | 30 | — | — | — | — | — |
| Normal Butane | | 6 | 6 | 42 | 48 | — | 48 |
| Butenes-2 | | 20 | — | — | — | — | — |
| Alkylate | | — | 125 | — | 125 | 125 | — |
| Dimer | | — | — | 7 | 7 | 7 | — |
| | Total | 787 | [770] | 49 | 819 | 132 | 48 |
| Isobutane | | 710 | 639 | 0 | 639 | 0 | 0 |
| Olefins | | 71 | 0 | 0 | 0 | 0 | 0 |
| (IC$_4$/Olefin vol) | | (10/1) | — | — | — | — | — |

| (B) | Field Butanes | Olefins | Olefins to Fractionation | Olefins By Pass | Fractionator Overhead | Fractionator Bottoms | Fresh Feed to Alkylation | Isobutane Recycle |
|---|---|---|---|---|---|---|---|---|
| OLEFIN COMPOSITION CHANGED WITHOUT INVENTION OPERATION (Same Division of Olefin) | | | | | | | | |
| Isobutane | 61 | 6 | 2 | 4 | 63 | — | 67 | 639 |
| Isobutylene | — | 24 | 8 | 16 | 8 | — | 24 | — |
| Butene-1 | — | 34 | 11.33 | 22.67 | 11.33 | — | 34 | — |
| Normal Butane | 39 | 6 | 2 | 4 | — | 41 | 4 | — |
| Butenes-2 | — | 30 | 10 | 20 | — | 10 | 20 | — |
| Alkylate | — | — | — | — | — | — | — | — |
| Dimer | — | — | — | — | — | — | — | — |
| Total | 100 | 100 | 33.33 | 66.67 | 82.33 | 51 | 149 | 639 |
| Isobutane | 61 | 6 | 2 | 4 | 63 | 0 | 67 | 639 |
| Olefins | 0 | 88 | 29.33 | 58.67 | 19.33 | 10 | 78 | — |
| (IC$_4$/Olefin vol) | — | — | | | | | | |

| (B) | | Total To Alkylation | Alky Yield | Dimer Yield | Total To Main Fractionation | Gasoline Yield | Normal Butane |
|---|---|---|---|---|---|---|---|
| OLEFIN COMPOSITION CHANGED WITHOUT INVENTION OPERATION (Same Division of Olefin) | | | | | | | |
| Isobutane | | 706 | 628 | — | 628 | — | — |
| Isobutylene | | 24 | — | — | — | — | — |
| Butene-1 | | 34 | — | — | — | — | — |
| Normal Butane | | 4 | 4 | 41 | 45 | — | 45 |
| Butenes-2 | | 20 | — | — | — | — | — |
| Alkylate | | — | 137.3 | — | 137.3 | 137.3 | — |
| Dimer | | — | — | 7 | 7 | 7 | — |
| | Total | 788 | [769.3] | 48 | 817.3 | 144.3 | 45 |
| Isobutane | | 706 | 628(a) | 0 | 628 | 0 | 0 |
| Olefins | | 78 | 0 | 0 | 0 | 0 | 0 |
| (IC$_4$/Olefin vol) | | (9.06/1) | | | | | |

| (C) | Field Butanes | Olefins | Olefins to Fractionation | Olefins By Pass | Fractionator Overhead | Fractionator Bottoms | Fresh Feed to Alkylation | Isobutane Recycle |
|---|---|---|---|---|---|---|---|---|
| OLEFIN COMPOSITION AS IN II WITH INVENTION'S OPERATION- (Typical to illustrate) | | | | | | | | |
| Isobutane | 61 | 6 | 4.8 | 1.2 | 65.8 | — | 67 | 653.2 |
| Isobutylene | — | 24 | 19.2 | 4.8 | 19.2 | — | 24 | — |
| Butene-1 | — | 34 | 27.2 | 6.8 | 27.2 | — | 34 | — |
| Normal Butane | 39 | 6 | 4.8 | 1.2 | — | 43.8 | 1.2 | — |
| Butenes-2 | — | 30 | 24 | 6 | — | 24 | 6 | — |
| Alkylate | — | — | — | — | — | — | — | — |
| Dimer | — | — | — | — | — | — | — | — |
| Total | 100 | 100 | 80 | 20 | 112.2 | 67.8 | 132.2 | 653.2 |
| Isobutane | 61 | 6 | 4.8 | 1.2 | 65.8 | 0 | 67 | 653.2 |
| Olefins | 0 | 88 | 70.4 | 17.6 | 46.4 | 24 | 64 | — |
| (IC$_4$/Olefin vol) | — | — | | | | | | |

| | Total To | Alky | Dimer | Total To Main | Gasoline | Normal |
|---|---|---|---|---|---|---|

EXAMPLE 3-continued (Barrels/Hour)

| (C) | | Alkylation | Yield | Yield | Fractionation | Yield | Butane |
|---|---|---|---|---|---|---|---|
| OLEFIN COMPOSITION AS IN II WITH INVENTION'S OPERATION- (Typical to illustrate) | | | | | | | |
| Isobutane | | 720.2 | 656.2 | — | 656.2 | — | — |
| Isobutylene | | 24 | — | — | — | — | — |
| Butene-1 | | 34 | — | — | — | — | — |
| Normal Butane | | 1.2 | 1.2 | 43.8 | 45 | — | — |
| Butenes-2 | | 6 | — | — | — | — | 45 |
| Alkylate | | — | 112.6 | — | 112.6 | 112.6 | — |
| Dimer | | — | — | 16.8 | 16.8 | 16.8 | — |
| | Total | 785.4 | 770 | 60.6 | 830.6 | 129.4 | 45 |
| Isobutane | | 720.2 | 656.2 | — | 656.2 | — | — |
| Olefins | | 64 | — | — | — | — | — |
| (IC$_4$/Olefin vol) | | (11.38) | — | — | — | — | — |

EXAMPLE 2

See FIG. 2.

Run I (A) is an initial operation wherein the total alkylate yield is 812 barrels per hour. Fresh or feed isobutane is 71 barrels per hour. Olefin feed is 81 barrels per hour. The olefin is split 19.5 percent to fractionation and 80.5 percent by-passed to alkylation giving the needed 71 barrels per hour olefin for alkylation. Ten barrels per hour olefin goes to dimerization. Total alkylation yield is 812 barrels per hour. Isobutane to olefin volume ratio is 10 to 1.

Run II (B) has an increase in olefin in the feed and does not use the invention. The same split of olefin is maintained as in Run I absent the invention. Feed isobutane is 67 barrels per hour. Olefin to alkylation is now 76.7 barrels per hour, or each hour 76.7–67 or 9.7 barrels per hour of recycle isobutane is used up. Ultimately recycle isobutane would be zero. In the first cycle or hour recycle isobutane falls about 9.7 barrels per hour. Total alkylate yield falls about 3 barrels per hour.

Run III (C) has the same increase in olefin as Run II, but applies the invention which maintains the total alkylate yield at 812 barrels per hour. Run III adjust the split of olefin between the fractionator and the by-pass to alkylation. Run III is an illustrative "spot" run. That is, as the amount of total alkylate yield tries to drop below 812 barrels per hour, less olefin is fed to alkylation, allowing isobutane recycle to increase to account for losses in feed to alkylation. In order for isobutane to build up, less olefin than the feed isobutane is charged to alkylation. This operation maintains the total alkylate yield at 812 barrels per hour. However, when the recycle isobutane tends to increase too much, the system increase the amount of olefin to alkylation, still maintaining 812 barrels per hour total alkylate yield to maximize use of feed isobutane and to maximize alkylation of butenes-2, known to produce high octane alkylate.

EXAMPLE 2

Now Preferred (Barrels/hour)

| (A) STREAM NUMBER COMPONENT (I) | | Field Butanes To Alky | Olefins | Olefins to Fractionation | Olefins By Pass | Fractionator Overhead | Fractionator Bottoms | Fresh Feed to Alkylation | Isobutane Recycle |
|---|---|---|---|---|---|---|---|---|---|
| Isobutane | | 61 | 10 | 1.9 | 8.1 | 62.9 | — | 8.1 | 701.9 |
| Isobutylene | | — | 21 | 4.1 | 16.9 | 4.1 | — | 16.9 | — |
| Butene-1 | | — | 30 | 5.9 | 24.1 | 5.9 | — | 24.1 | — |
| Normal Butane | | 39 | 9 | 1.7 | 7.3 | — | 40.7 | 48 | — |
| Butenes-2 | | — | 30 | 5.9 | 24.1 | — | 5.9 | 30 | — |
| Alkylate | | — | — | — | — | — | — | — | — |
| Dimer | | — | — | — | — | — | — | — | — |
| | Total | 100 | 100 | 19.5 | 80.5 | 72.9 | 46.6 | 127.1 | 701.9 |
| Isobutane | | 61 | 10 | 2 | 8 | 62.9 | 0 | 8.1 | 701.9 |
| Olefins | | 0 | 81 | 15.7 | 65.3 | 10 | 5.9 | 71 | 0 |
| (IC$_4$/Olefin vol) | | — | — | — | — | — | — | — | — |

| (A) STREAM NUMBER COMPONENT (I) | | Total To Alkylation | Alky Yield | Dimer Yield | Total To Main Fractionation | Gasoline Yield | Normal Butane |
|---|---|---|---|---|---|---|---|
| Isobutane | | 710 | 639 | 62.9 | 701.9 | — | — |
| Isobutylene | | 16.9 | — | — | — | — | — |
| Butene-1 | | 24.1 | — | — | — | — | — |
| Normal Butane | | 48 | 48 | — | 48 | — | 48 |
| Butenes-2 | | 30 | — | — | — | — | — |
| Alkylate | | — | 125 | — | 125 | 125 | — |
| Dimer | | — | — | 7 | 7 | 7 | — |
| | Total | 829 | 812 | 69.9 | 881.9 | 132 | 48 |
| Isobutane | | | | 62.9 | 701.9 | 0 | 0 |
| Olefins | | | | 0 | — | 0 | 0 |
| (IC$_4$/Olefin vol) | | (10/1) | — | — | — | — | — |

(B)

EXAMPLE 2-continued

Now Preferred (Barrels/hour)

| OLEFIN COMPOSITION CHANGED WITHOUT INVENTION OPERATION (Same Division of Olefin) | Field Butanes To Alky | Olefins | Olefins to Fractionation | Olefins By Pass | Fractionator Overhead | Fractionator Bottoms | Fresh Feed to Alkylation | Isobutane Recycle |
|---|---|---|---|---|---|---|---|---|
| Isobutane | 61 | 6 | 1.2 | 4.8 | 62.2 | — | 4.8 | 701.9 |
| Isobutylene | — | 24 | 4.7 | 19.3 | 4.7 | — | 19.3 | — |
| Butene-1 | — | 34 | 6.6 | 27.4 | 6.6 | — | 27.4 | — |
| Normal Butane | 39 | 6 | 1.2 | 4.8 | — | 40.2 | 45 | — |
| Butenes-2 | — | 30 | 5.9 | 24.1 | — | 5.9 | 30 | — |
| Alkylate | — | — | — | — | — | — | — | — |
| Dimer | — | — | — | — | — | — | — | — |
| Total | 100 | 100 | 19.6 | 80.4 | 73.5 | 46.1 | 126.5 | 701.9 |
| Isobutane | 61 | 6 | 1.2 | 4.8 | 62.2 | 0 | 4.8 | 701.9 |
| Olefins | 0 | 88 | 17.2 | 70.8 | 11.3 | 5.9 | 76.7 | 0 |
| (IC₄/Olefin vol) | — | — | | | | | | |

| (B) OLEFIN COMPOSITION CHANGED WITHOUT INVENTION OPERATION (Same Division of Olefin) | Total To Alkylation | Alky Yield | Dimer Yield | Total To Main Fractionation | Gasoline Yield | Normal Butane |
|---|---|---|---|---|---|---|
| Isobutane | 705.7 | 628.8 | 62.2 | 691 | — | — |
| Isobutylene | 19.3 | — | — | — | — | — |
| Butene-1 | 27.4 | — | — | — | — | — |
| Normal Butane | 45 | 45 | — | 45 | — | 45 |
| Butenes-2 | 30 | — | — | — | — | — |
| Alkylate | — | 135 | — | 135 | 135 | — |
| Dimer | — | — | 7.9 | 7.9 | 7.9 | — |
| Total | 827.2 | 808.8 | 70.1 | 878.9 | 142.9 | 45 |
| Isobutane | 705.7 | 628.8 | 62.2 | 691 | 0 | |
| Olefins | 76.7 | 0 | 0 | 0 | 0 | |
| (IC₄/Olefin vol) | (9.2/1) | — | — | — | — | |

EXAMPLE 3

NOW PREFERRED (Barrels/Hour)

| (C) OLEFIN COMPOSITION CHANGED WITH INVENTION'S OPERATION | Field Butanes To Alky | Olefins | Olefins to Fractionation | Olefins By Pass | Fractionator Overhead | Fractionator Bottoms | Fresh Feed to Alkylation | Isobutane Recycle |
|---|---|---|---|---|---|---|---|---|
| Isobutane | 61 | 6 | 3 | 3 | 64 | — | 3 | 722.2[a] |
| Isobutylene | — | 24 | 12 | 12 | 12 | — | 12 | — |
| Butene-1 | — | 34 | 17 | 17 | 17 | — | 17 | — |
| Normal Butane | 39 | 6 | 3 | 3 | — | 42 | 45 | — |
| Butenes-2 | — | 30 | 15 | 15 | — | 15 | 30 | — |
| Alkylate | — | — | — | — | — | — | — | — |
| Dimer | — | — | — | — | — | — | — | — |
| Total | 100 | 100 | 50 | 50 | 93 | 57 | 107 | 722.2 |
| Isobutane | 61 | 6 | 3 | 3 | 64 | 0 | 3 | 722.2 |
| Olefins | 0 | 88 | 44 | 44 | 29 | 15 | 59 | 0 |
| (IC₄/Olefin vol) | — | — | — | — | — | — | — | — |

| (C) OLEFIN COMPOSITION CHANGED WITH INVENTION'S OPERATION | Total To Alkylation | Alky Yield | Dimer Yield | Total To Main Fractionation | Gasoline Yield | Normal Butane |
|---|---|---|---|---|---|---|
| Isobutane | 725.2 | 663.2 | 64 | 727.2 | — | — |
| Isobutylene | 12 | — | — | — | — | — |
| Butene-1 | 17 | — | — | — | — | — |
| Normal Butane | 45 | 45 | — | 45 | — | 45 |
| Butenes-2 | 30 | — | — | — | — | — |
| Alkylate | — | 103.8 | — | 103.8 | 103.8 | — |
| Dimer | — | — | 20.3 | 20.3 | 20.3 | — |
| Total | 829.2 | 812 | 84.3 | 896.3 | 124.1 | 45 |
| Isobutane | 725.2 | | | | | |
| Olefins | 59 | | | | | |
| (IC₄/Olefin vol) | (12.29/1) | | | | | |

[a] Feed IC₄ of 64 included

Reasonable variation and modification are possible within the scope of the foregoing disclosure, drawings and the appended claims to the invention, the essence of which is that there has been set forth a process for the alkylation of an isoparaffin with an olefin which comprises, in a broad form thereof, achieving maximum utilization of isoparaffin by detecting and/or measuring the amount of alkylated hydrocarbon effluent, the alkylation zone and controlling the olefin feed to said zone responsive to any change in said amount to maintain in said zone the desired ratio of isoparaffin to olefin; for example, when the amount of hydrocarbon effluent said zone is decreasing, indicating a reduction of isoparaffin to olefin ratio, reducing the proportion of olefin fed to said zone, and vice versa when the hydrocarbon effluent said zone is increasing.

I claim:

1. A process for the alkylation of a feed isoparaffin and an olefin which comprises feeding into an alkylation zone, maintained under alkylation conditions, said feed isoparaffin and an olefin, and achieving maximum utilization of isoparaffin by feeding at a maximum available rate of flow said feed isoparaffin to said alkylation zone and maintaining said rate of flow throughout the operation described in this claim, detecting or measuring the amount of alkylated hydrocarbon effluent the alkylation zone and controlling the olefin to said alkylation zone responsive to any change in said amount to maintain in said alkylation zone the desired ratio of isoparaffin to olefin without changing said rate of flow so that when the amount of hydrocarbon effluent said zone is decreasing, indicating a reduction of isoparaffin to olefin ratio, the proportion of olefin fed to said alkylation zone is reduced and vice versa when the hydrocarbon effluent said zone is increasing.

2. A process according to claim 1 wherein an olefin feed is divided into at least two portions, one of which is fed to said alkylation zone as said olefin fed to said zone and the other of which is fed to a dimerization zone, maintained under dimerization conditions, the olefin is dimerized in said zone and dimer thus obtained is combined with the hydrocarbon effluent said alkylation zone.

3. A process according to claim 2 where the isoparaffin fed to the alkylation zone is comprised in a stream containing a substantial proportion of isoparaffin but also containing other hydrocarbons and the olefin fed to said alkylation zone is comprised in a stream which in addition to containing at least one olefin also contains isoparaffin and wherein the effluent from the alkylation zone and from the dimerization zone are fractionated to recover a product containing alkylate and dimer and an isoparaffin containing stream, and said isoparaffin containing stream is recycled to the alkylation zone.

4. A process according to claim 3 wherein provision is made to fractionate the isoparaffin containing stream and as required, the olefin containing stream in a fractionation zone, lighter olefin from said zone is passed to dimerization along with some isoparaffin, olefin feed is passed directly to said alkylation, bottoms from said fractionation zone are also passed through said alkylation and when olefin passing to said alkylation is needed to be reduced a portion of the bottoms is diverted to said dimerization zone.

5. A process according to claim 1 wherein a liquid acid catalyst is employed in said alkylation zone, the alkylation effluent is passed to a settling zone, acid separating in said zone is maintained on liquid level control, the level of supernatant hydrocarbon phase is sensed and the total amount of olefin fed to said alkylation zone is controlled responsive to change in said level to maintain said level substantially constant while all isoparaffin obtained as recycle is passed to said alkylation zone together with said feed isoparaffin fed at said rate of flow which is maintained.

6. A process according to claim 5 which comprises providing a fractionation zone for fractionating an isoparaffin containing stream and an olefin containing stream, containing some isoparaffin, as it may be desired, overhead from said fractionation is passed primarily to a dimerization zone but can also be passed at least in part to said alkylation zone, bottoms from said fractionation zone are passed to said alkylation zone at least in part, but may also be passed to said dimerization zone and are so passed to said dimerization zone, and when the hydrocarbon effluent said alkylation zone is increasing the flow of olefin to said alkylation zone is increased, and vice versa.

* * * * *